United States Patent [19]
Watanabe et al.

[11] Patent Number: 5,817,639
[45] Date of Patent: Oct. 6, 1998

[54] PURINE 4'-THIOARABINONUCLEOSIDES

[75] Inventors: Mikari Watanabe, Choshi; Yuichi Yoshimura, Hasaki-machi; Shinji Sakata, Choshi; Noriyuki Ashida, Fukushima; Haruhiko Machida, Choshi, all of Japan

[73] Assignee: Yamasa Corporation, Chiba, Japan

[21] Appl. No.: 679,448

[22] Filed: Jul. 12, 1996

[30] Foreign Application Priority Data

Jul. 14, 1995 [JP] Japan ................... 7-201579
Jan. 11, 1996 [JP] Japan ................... 8-20412

[51] Int. Cl.⁶ ............... A61K 31/70; C07H 1/00; C07H 19/09; C07H 19/19
[52] U.S. Cl. .................. 514/45; 514/46; 514/47; 514/49; 514/50; 514/931; 514/934; 536/4.1; 536/27.1; 536/27.13; 536/27.21; 536/27.6; 536/27.61; 536/27.63; 536/27.7; 536/27.81; 536/28.1; 536/28.5; 536/28.52; 536/28.53; 536/28.54; 536/28.55; 549/30; 549/31; 549/33
[58] Field of Search .................. 514/46, 47, 45, 514/49, 50, 931, 934; 536/27.4, 27.61, 27.62, 27.63, 27.7, 22.8, 27.81, 4.1, 27.1, 27.13, 27.21, 27.6, 28.1, 28.5, 28.52, 28.53, 28.54, 28.55; 549/30, 31, 33

[56] References Cited

U.S. PATENT DOCUMENTS 3,956,277  5/1976  Elion et al. .................. 536/27.4
5,591,722  1/1997  Montgomery et al. .......... 514/45

OTHER PUBLICATIONS

J. of Org. Chem., vol. 33, No. 1, pp. 189–192, 1968.
Anisuzzaman et al., J. Bangladesh Acad. Sci., vol. 2, No. 2, pp. 59–64 (1978). HCAPLUS Abstract.

*Primary Examiner*—James D. Wilson
*Attorney, Agent, or Firm*—Wenderoth, Lind & Ponack, L.L.P.

[57] ABSTRACT

The present invention provides a novel purine 4'-thioarabinonucleoside represented by the following formula [1]:

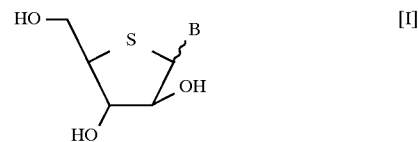

wherein B represents a purine base other than adenine. Also disclosed are a method for preparing the purine 4'-thioarabinonucleoside and pharmaceutical compositions containing the purine 4'-thioarabinonucleoside.

9 Claims, No Drawings

PURINE 4'-THIOARABINONUCLEOSIDES

BACKGROUND OF THE INVENTION

1. Field of the Invention

The present invention relates to purine 4'-thioarabinonucleosides.

2. Related Art

The only purine 4'-thioarabinonucleoside reported heretofore is 9-(4-thio-β-D-arabinofuranosyl)adenine disclosed in J. Org. Chem., 33(1), pp. 189–192, 1968. However, that journal does not describe the biological activities of this compound.

Thus, it can be seen that purine 4'-thioarabino-nucleosides have scarcely been studied thus far. Therefore, it was considered that purine 4'-thioarabinonucleosides having biological activities superior to those possessed by previously known 4'-thioarabinonucleoside might be discovered.

SUMMARY OF THE INVENTION

Under the aforementioned circumstances, we conducted careful research to achieve the above object and found that a variety of purine 4'-thioarabinonucleosides can be easily obtained in a reduced number of reaction steps by the use of the novel synthesis method we developed, and that the resultant compounds have antiviral activities. The present invention was achieved based on these findings.

Accordingly, an object of the present invention is to provide a novel class of purine 4'-thioarabinonucleosides and a method for synthesizing these compounds.

In one aspect of the present invention, there is provided purine 4'-thioarabinonucleoside represented by the following formula [I]:

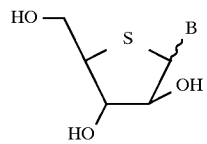

wherein B represents a purine base other than adenine.

In another aspect of the present invention, there is provided a method for preparing purine 4'-thioarabinonucleoside of formula [I] comprising steps 1 through 4 described below.

Step 1:

In step 1, a sulfonyl group is introduced to each of the 2- and 5- positions of a compound of formula [II], after which the compound is reacted with a sulfide to obtain a compound represented by formula [III]:

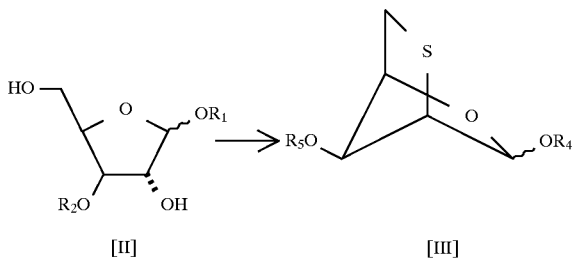

wherein $R_1$ represents an alkyl group and $R_2$ represents a protective group for a hydroxyl group.

Step 2:

The furanose ring of the compound represented by formula [III] is hydrolyzed and then reduced to obtain a compound represented by formula [IV]:

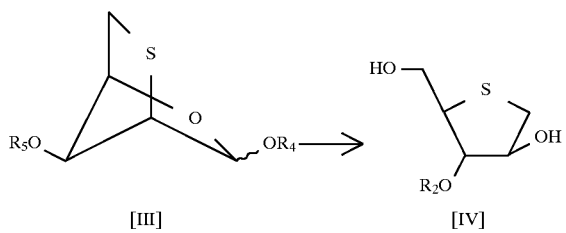

wherein $R_1$ and $R_2$ have the same meanings as defined above.

Step 3:

The compound of formula [IV], while the hydroxyl groups at the 2- and 5- positions of the compound are protected, is reacted with an oxidizing agent to form a sulfoxide. The sulfoxide is converted into a compound of formula [V] through Pummerer rearrangement:

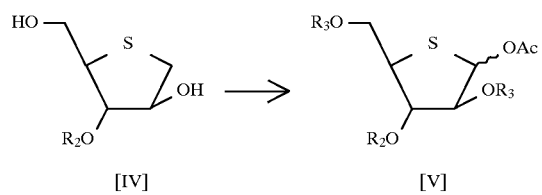

wherein Ac represents an acetyl group and each of $R_2$ and $R_3$ represents a protective group for a hydroxyl group.

Step 4:

The compound of formula [V] is subjected to a glycosylation reaction so as to introduce a purine base represented by B to the 1- position of the saccharide moiety, after which the protective groups for the hydroxyl groups in the saccharide moiety are eliminated to obtain a compound of formula [II]:

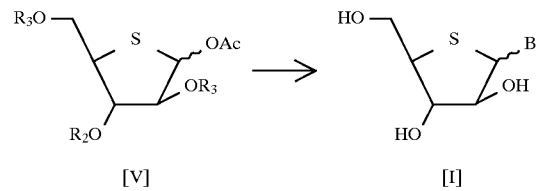

wherein Ac, $R_2$, $R_3$, and B have the same meanings as defined above.

In still another aspect of the present invention, there is provided a pharmaceutical composition comprising purine 4'-thioarabinonucleoside represented by the above-described formula [I] as an active ingredient.

The other objects, features, and advantages of the present invention will become apparent from the following description.

DESCRIPTION OF PREFERRED EMBODIMENTS

The present invention will next be described in detail.

(1) Compounds

The compounds of the present invention are represented by formula [I] described above. Purine bases represented by B in the formula encompass, in addition to well-known bases of nucleic acid such as guanine and hypoxanthine excepting adenine, azapurine derivatives (8-azapurine, 2-azapurine, etc.) and deazapurine derivatives (3-deazapurine, 7-deazapurine, etc.). B may have one or a plurality of substituents (such as lower (C1–C5) alkyl, halogen, amino, alkoxy, etc.) as a result of introduction of these substituents to one or more arbitrary positions of the above-mentioned bases including adenine. Specific examples of bases having such substituents include, but are not limited to, 2-aminopurine, 2,6-diaminopurine, 6-chloropurine, 6-chloro-2-aminopurine, 6-methoxypurine, 6-methoxy-2-aminopurine, and 6-cyclopropylmethylamino-2-aminopurine.

The compounds of the present invention may take the forms of salts, hydrates, or solvates. Examples of the salts include acid addition salts formed in combination with inorganic acids (hydrochloric acid, sulfuric acid, phosphoric acid, etc.) or organic acids (fumaric acid, tartaric acid, succinic acid, etc.).

The hydrates and solvates may be those in which 0.1–3.0 molecules of water or a solvent is added to 1 molecule of the compound of the present invention or a salt thereof. Also, the compounds of the present invention encompass a variety of isomers such as α-anomers, β-anomers, and tautomers.

Particularly preferred are 9-glycosylated compounds of the β-anomer type. Specific examples of preferred compounds of the present invention include the following:

9-(4-thio-β-D-arabinofuranosyl)guanine
9-(4-thio-β-D-arabinofuranosyl)hypoxanthine
9-(4-thio-β-D-arabinofuranosyl)-2-aminopurine
9-(4-thio-β-D-arabinofuranosyl)-2,6-diaminopurine
9-(4-thio-β-D-arabinofuranosyl)-6-chloropurine
9-(4-thio-β-D-arabinofuranosyl)-6-chloro-2-aminopurine,
and
9-(4-thio-β-D-arabinofuranosyl)-6-methoxy-2-aminopurine.

(2) Process of Manufacture

The compounds of the present invention are synthesized through the following 4 steps.

Step 1:

In Step 1 of the method of the present invention, a sulfonyl group is introduced to each of the 2- and 5- positions of a compound of formula [II], after which the compound is reacted with a sulfide to obtain a compound represented by formula [III]:

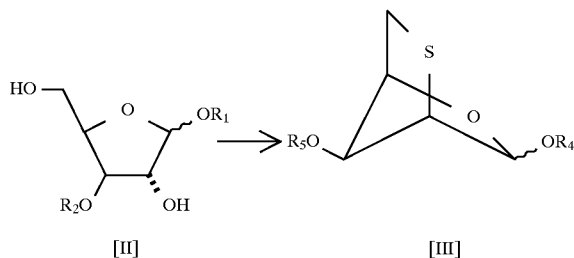

[II]                                [III]

wherein $R_1$ represents an alkyl group and $R_2$ represents a protective group for a hydroxyl group.

The starting material used in the method of the present invention is a xylose derivative (hereinafter may be referred to as the starting compound) represented by formula [II].

Examples of the alkyl group represented by $R_1$ include C1–C3 lower alkyl groups such as methyl and ethyl, and substituted or unsubstituted benzyl groups such as benzyl and methoxy benzyl.

The protective group for the hydroxyl group represented by $R_2$ is not particularly limited so long as it is selected from those which are generally used. Specific examples of the protective group include alkyl groups, silyl groups, and acyl groups. More specifically, alkyl groups which may be used for the purpose of protection include those listed for $R_1$. Examples of silyl groups include t-butyldimethylsilyl, t-butyldiphenylsilyl, etc., and examples of acyl groups include acetyl, benzoyl, pivaloyl, etc.

The starting compound of the method of the present invention may be prepared using a well-known method such as the one described in Tetrahedron, 37, pp. 2379–2382 (1981), the content of which is incorporated herein by reference.

Examples of the sulfonyl group which is introduced into the hydroxyl groups at the 2- and 5- positions of the compound of formula [II] include mesyl and tosyl.

A mesylation reaction and tosylation reaction may be performed using conventional methods. For example, mesylation reaction may be performed as follows. One mole of a starting compound is reacted with 2–10 mols, preferably 2–4 mols, of mesyl halide (e.g., mesyl chloride) at 0–100° C. for 0.5–5 hours while stirring in the presence of a base such as triethylamine in an organic solvent such as methylene chloride, acetonitrile, dimethylformamide, or pyridine (when pyridine is used as the organic solvent, a base such as triethylamine is not necessarily used). The reaction is preferably performed in an atmosphere of an inert gas such as argon or nitrogen.

Subsequently, the thus-obtained compound is reacted with a sulfide to afford a compound of formula [III].

The sulfide used in this reaction is not particularly limited as long as it is a metal sulfide (preferably, alkali metal sulfide) such as sodium sulfide, potassium sulfide, etc.

The reaction may be performed by reacting 1 mol of a starting compound with 1–20 mols of a sulfide at a temperature between room temperature and 150° C. for 0.5–5 hours while stirring in an organic solvent such as dimethylformamide, dimethylsulfoxide, etc. When necessary, the reaction may be performed in an atmosphere of an inert gas such as argon or nitrogen.

The thus-produced compound of formula [III] may be separated and purified using conventional means for the separation and purification of protected saccharides. For example, the mixture may be partitioned using ethyl acetate and water, after which silica gel column chromatography may be performed using an organic solvent mixture for elution such as n-hexane-ethyl acetate, thereby separating and purifying the formula [III] compound.

Step 2:

In Step 2 of the method of the present invention, the furanose ring of the compound represented by formula [III] is hydrolyzed and then reduced to obtain a compound represented by formula [IV]:

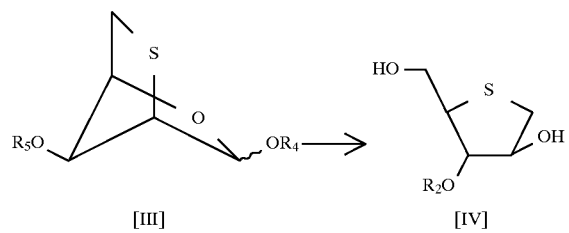

[III]                                [IV]

wherein $R_1$ and $R_2$ have the same meanings as defined above.

The method of hydrolysis is not particularly limited so long as the furanose ring of the compound of formula [III] can be hydrolyzed by the method. Methods using acid catalysts are particularly preferred.

Examples of acid catalysts include inorganic acids such as hydrochloric acid, sulfuric acid, etc. and organic acids such as acetic acid and trifluoroacetic acid.

The hydrolysis reaction may be performed in a water-soluble ether-derived solvent such as tetrahydrofuran, dioxane, etc. in the presence of any one of the above-mentioned acid catalysts between room temperature and 100° C. for 0.5–5 hours while stirring.

When the thus-obtained compound is subjected to a reduction reaction, a compound of formula [IV] is obtained.

Examples of reducing agents include tetrahydroborates such as sodium tetrahydroborate (sodium borohydride), potassium tetrahydroborate, etc.

The reduction reaction may be performed by reacting 1 mol of a compound of formula [III] with 0.2–10 mols of a reducing agent in an alcoholic solvent such as methanol at a temperature between −80 and 100° C. for 0.5–3 hours while stirring.

The thus-obtained formula [IV] compound may be separated and purified using conventional means for the separation and purification of protected saccharides. For example, neutralization of the reaction mixture at the completion of reaction, evaporation of the organic solvent, extraction using chloroform, and silica gel column chromatography may serially be performed so as to obtain the target compound as a separated and purified product.

Step 3:

In Step 3 of the method of the present invention, the compound of formula [IV] is reacted with an oxidizing agent while protecting the hydroxyl groups at the 2- and 5- positions of the compound to form a sulfoxide. Subsequently, the sulfoxide is converted into a compound of formula [V] through Pummerer rearrangement.

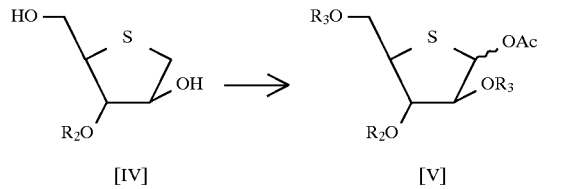

wherein Ac represents an acetyl group and each of $R_2$ and $R_3$ represents a protective group for a hydroxyl group.

Examples of the protective groups represented by $R_3$ and introduced to the 2- and 5- positions of the compound of formula [IV] include lower alkyl groups such as methyl and ethyl; substituted or unsubstituted benzyl groups such as benzyl and dimethoxybenzyl; silyl groups such as t-butyldimethylsilyl and t-butyldiphenylsilyl; and acyl groups such as acetyl, benzoyl, and pivaloyl.

Protective groups may be introduced by routine methods. For example, protective groups may be introduced by reacting 1 mol of a compound of formula [IV] with 2–10 mols, preferably 3–8 mols, of an alkylating agent such as benzyl chloride, benzyl bromide, or p-methoxybenzyl chloride in a single organic solvent such as dimethylformamide, dimethylsulfoxide, etc. or in a solvent mixture such as tetrahydrofuran-dimethylsulfoxide in the presence of a base such as sodium hydride in an atmosphere of an inert gas such as argon, nitrogen, etc. at 0–50° C. overnight while stirring.

Examples of the oxidizing agent used in the oxidizing reaction include m-chloroperbenzoic acid and sodium metaperiodate.

The oxidizing reaction may be performed by reacting 1 mol of a compound of formula [IV] in which the hydroxyl groups at the 2- and 5- positions are protected with 0.2–5 mols of an oxidizing agent (such as m-chloroperbenzoic acid, sodium metaperiodate, etc.) in an organic solvent such as methylene chloride or alcohol (e.g., methanol) in a stream of an inert gas such as argon or nitrogen, if necessary, at a temperature between −100 and 0° C. for 10 minutes to 2 hours.

When the thus-obtained sulfoxide is subjected to a Pummerer rearrangement reaction, a compound of formula [V] is obtained.

The Pummerer rearrangement reaction may be performed by a conventional method. For example, the sulfoxide is stirred for 1–5 hours between 60° C. and the refluxing temperature in an acid anhydride such as acetic anhydride.

The thus-obtained formula [V] compound may be separated and purified using conventional separation and purification techniques. For example, neutralization, evaporation of the organic solvent, extraction from the aqueous layer using chloroform, and silica gel column chromatography may sequentially be performed so as to obtain the formula [V] compound as a separated and purified product.

If a purification step is required to be performed before oxidation reaction, the mixture may be partitioned using ethyl acetate and water, after which silica gel column chromatography may be performed using an organic solvent mixture for elution such as n-hexane-ethyl acetate, thereby separating and purifying the formula [V] compound.

Step 4:

In Step 4 of the method of the present invention, the compound of formula [V] is subjected to a glycosylation reaction so as to introduce a base represented by B to the 1-position of the saccharide moiety, after which the protective groups for the hydroxyl groups in the saccharide moiety are eliminated to obtain a compound of formula [I].

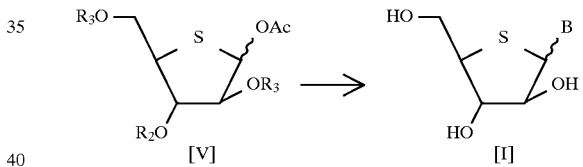

wherein Ac, $R_2$, $R_3$, and B have the same meanings as defined hereinbefore.

Specific examples of Lewis acids used in the glycosylation reaction include, but are not limited to, trimethylsilyl trifluoromethane sulfonate, tin tetrachloride, titanium tetrachloride, zinc chloride, zinc iodide, and boron trifluoride.

The glycosylation reaction may be performed by reacting 1 mol of a compound of formula [IV] with 1–10 mols of a base of nucleic acid and 0.1–10 mols of any one of the aforementioned Lewis acids in an organic solvent such as methylene chloride, chloroform, dichloroethane, acetonitrile, or dimethylformamide in a stream of an inert gas such as argon or nitrogen at a temperature between −50 and 100° C. for 1–3 hours. If a silylated base of nucleic acid is used, 7-glycosylated compounds can be synthesized with priority.

Subsequently, when the protective group for the hydroxyl group in the saccharide moiety is eliminated, a compound of formula [I] is obtained.

The elimination of the groups protecting the hydroxyl groups may be suitably performed by hydrolysis, catalytic hydrogenation, or any other conventional process in accordance with the protective groups used. For example, when the protective groups are benzyl groups or benzyl-derived groups, they are eliminated through reaction with boron trichloride for between 10 minutes and 6 hours at a temperature between −100 and 50° C. in methylene chloride in a stream of an inert gas such as argon or nitrogen.

The thus-obtained compound [I] may be separated and purified by a suitable combination of conventional separation and purification methods (recrystallization, a variety of column chromatography procedures, etc.) for nucleosides.

(3) Use

Since the compounds of the present invention exhibit excellent antiviral activities, pharmaceutical compositions containing the compounds as active ingredients are useful for the prevention or the treatment of subjects who have been infected with a virus or who run the risk of infection with a virus.

Examples of target viruses include herpes simplex virus type 1 (hereinafter referred to as HSV-1), herpes simplex virus type 2 (hereinafter referred to as HSV-2), human cytomegalovirus (hereinafter referred to as HCMV), and varicella zoster virus (hereinafter referred to as VZV), all of which belong to the herpes virus family.

The dosage of the compound of formula [I], an active ingredient of the pharmaceutical composition of the present invention, varies depending on the patient's age and body weight, identity of disease, severity of disease, tolerance to the drug, manner of administration, etc. Therefore, the dose is determined considering these factors as a whole so as to be suited to the patient. Generally, the dose is between 0.001 and 1,000 mg/kg body weight, and preferably between 0.1 and 100 mg/kg body weight, per day, and is administered at a single treatment or in plural doses.

The manner of administration is not limited, and may be peroral, parenteral, enteral, or topical administration.

When pharmaceutical compositions containing the compound of the present invention are formulated, it is a general practice to incorporate ordinarily employed carriers, vehicles, and other additives. Carriers may be either solid or liquid. Examples of solid carriers include lactose, kaolin, sucrose, crystalline cellulose, cornstarch, talc, agar, pectin, stearic acid, magnesium stearate, lecithin, and sodium chloride; and examples of liquid carriers include glycerol, peanut oil, polyvinyl pyrrolidone, olive oil, ethanol, benzyl alcohol, propylene glycol, and water.

The compositions may take arbitrary forms. For example, if a solid carrier is used, tablets, powders, granules, capsules, suppositories, lozenges, etc. may be formed, and if a liquid carrier is used, syrups, emulsions, soft gelatin capsules, creams, gels, pastes, sprays, injections, etc. may be formed.

The compounds of the present invention are expected to be developed and used as medicinal agents due to their remarkable antiviral activities. Moreover, the method of the present invention is particularly useful for the manufacture of purine 4'-thioarabinonucleoside because firstly it employs an inexpensive substance as a starting material, secondly it requires a reduced number of steps, and thirdly its procedure is simple and easy.

EXAMPLES:

The present invention will next be described by way of example. However, the invention should not be construed as being limited by any of the examples.

Example 1:

Synthesis of [Ia-α]9-(4-thio-α-D-arabinofuranosyl)-2,6-diaminopurine and [Ia-β]9-(4-thio-β-D-arabinofuranosyl)-2,6-diaminopurine (in formula [I], B=2,6-diaminopurine):

1) Synthesis of 2,5-anhydro-3-O-benzyl-1-O-methyl-2-thio-β-D-arabinofuranose (formula [III], $R_1$=Me, $R_2$=Bn)

While cooling on ice, methanesulfonyl chloride (6.33 ml) was added to 80 ml of pyridine in which 3-O-benzyl-1-O-methyl-β-D-xylofuranose (6.93 g, formula [II], $R_1$=Me, $R_2$=Bn) had been dissolved. The mixture was stirred for 1 hour at room temperature under a flow of argon. Reaction was stopped by adding ice-water, after which the solvent was evaporated. The residue was partitioned using ethyl acetate-water, and the organic layer was dried. The solvent was evaporated, and the residue was dissolved in dimethylformamide (DMF, 100 ml). Sodium sulfide (9.84 g) was added, and the mixture was stirred for 1 hour at 100° C. under a flow of argon. The solvent was evaporated, and the residue was partitioned using ethyl acetate-water. The organic layer was washed using water and then dried. The solvent was evaporated and the residue was purified by silica gel column chromatography. The fraction eluted with 5–10% ethyl acetate-n-hexane was collected and concentrated to obtain 5.05 g of the target compound (yield 73%).

$^1$H—NMR (CDCl$_3$) δ 7.36–7.29 (5H, m), 4.89 (1H, s), 4.62 (1H, d, J=11.7 Hz), 4.52–4.48 (2 H, m), 4.37–4.36 (1H, m), 3.34 (4H, s), 3. 04 (1H, dd, J=10.3, 2.0 Hz), 2.77 (1H, dd, J=10.3, 1.5 Hz)

2) Synthesis of 2,5-anhydro-3-O-benzyl-1-O-methyl-2-thio-α-D-arabinofuranose (formula [III], $R_1$=Me, $R_2$=Bn)

The procedure of 1) was repeated using 3-O-benzyl-1-O-methyl-α-D-xylofuranose (6.13 g, formula [II], $R_1$=Me, $R_2$=Bn) instead of 3-O-benzyl-1-O-methyl-β-D-xylofuranose , thereby obtaining 4.75 g of the target compound (yield 42%).

$^1$H—NMR (CDCl$_3$) δ7.39–7.30 (5H, m), 5.13 (1H, d, J=2.4 Hz), 4.66 (1H, d, J=11.7 Hz), 4.5 3 (1H, d), 4.36–4.35 (1H, brm), 4.29 (1H, t, J=2.4 Hz), 3.51 (1H, t, J=2.4 Hz), 3.47 (3H, s), 3.04 (1H, dd, J=10.5, 2.2 Hz), 2.95 (1H, dd, J=10.5, 1.2 Hz)

3) Synthesis of 3-O-benzyl-1-deoxy-4-thio-D- arabinofuranose (formula [IV] , $R_2$=Bn)

2,5-Anhydro-3-O-benzyl-1-O-methyl-2-thio-D- arabinofuranose (9.50 g, α:β=1:1) was dissolved in tetrahydrofuran (THF, 200 ml). To the solution was added 4N—HCl (100 ml), and the mixture was stirred for 1 hour at room temperature. The reaction mixture was neutralized using solid sodium hydrogencarbonate. Insoluble matter was removed by filtration, after which THF was evaporated under reduced pressure. Extraction was performed three times using chloroform, and the organic layer was dried. The solvent was evaporated, and the residue was dissolved in methanol (150 ml). While cooling on ice, a methanol solution containing 1.43 g of sodium borohydride was added dropwise. After completion of addition, the mixture was stirred for 45 minutes while being cooled on ice. The reaction mixture was neutralized using acetic acid, after which the solvent was evaporated and the residue was partitioned using chloroform-water. The aqueous layer was extracted twice using chloroform, and the organic layer was dried. The solvent was evaporated, and the residue was subjected to silica gel column chromatography. The fraction eluted with 33–50% ethyl acetate-n-hexane was collected and concentrated to obtain 8.18 g of 3-O-benzyl-1-deoxy -4-thio-D-arabinofuranose (yield: 90%).

$^1$H—NMR (CDCl$_3$—D$_2$O) δ7.38–7.27 (5H, m) , 4.6 4 (2H, s) , 4.38 (1H, dt, J=2.9, 4.4 Hz), 3.96 (1H, t, J=2.9 Hz), 3.78 (1H, dd, J=2.9, 11.7 Hz), 3.66 (1H, dd, J=3.9, 11.7 Hz), 3.60 (1H, dt, J=2.9, 3.9 Hz), 3.21 (1H, dd, J=4.4, 11. 2 Hz), 2.90 (1H, dd, J=2.9, 11.2 Hz)

4) Synthesis of 1-O-acetyl-2,3,5-tri-O-benzyl-4-thio-D-arabinofuranose (formula [V], $R_2=R_3=Bn$)

3-O-Benzyl-1-deoxy-4-thio-D-arabinofuranose (5.0 g, 20.8 mmol) was dissolved in dimethylformamide (100 ml). To the solution was added 60% sodium hydride (4.16 g, 104 mmol) under a flow of argon, and the mixture was stirred for 1 hour at 0° C. After the one hour of stirring, benzyl chloride (16.8 ml, 146 mmol) in dimethylformamide (52 ml) was added dropwise. The resultant mixture was stirred overnight at room temperature and subsequently poured into ice-water so as to stop the reaction.

The mixture was partitioned using ethyl acetate. The organic layer was washed with saturated brine and then dried over sodium sulfate. The solution was concentrated and purified by silica gel column chromatography (AcOEt: Hex =1:6), thereby obtaining 5.54 g of 1-O-deoxy-2,3,5-tri-O-benzyl-4-thio-D-arabinofuranose (yield: 63.3%).

Elementary analysis: for $C_{26}H_{28}O_3S$

Calculated C: 74.25, H: 6.71

Found C: 74.28, H: 6.82

$^1$H–NMR (CDCl$_3$) δ7.35–7.25 (15H, m) , 4.90 (1H m), 4.72–4.45 (6H, m), 4.11 (1H, m), 3. 69 (1H, dd, J=7.3, 8.8 Hz), 3.56 (1H, ddd, J=3.4, 6.4, 7.3 Hz), 3.50 (1H, dd, J=6.4, 8.8 H z), 3.08 (1H, dd, J=4.9, 11.2 Hz), 2.90 (1H, dd, J=4.4, 11.2 Hz)

The resultant tribenzyl derivative (2.88 g, 6.85 mmol) was dissolved in distilled methylene chloride (40 ml). To the solution was added dropwise 80% m-chloroperbenzoic acid (1.48 g, 6.85 mmol) dissolved in distilled methylene chloride (40 ml) while maintaining the temperature at −78° C. under a flow of argon. The mixture was stirred for 30 minutes, and then the reaction was stopped using a saturated aqueous sodium hydrogen carbonate solution.

Subsequently, the mixture was extracted with methylene chloride, and the organic layer was washed once with a 10% sodium thiosulfate solution, twice with a saturated aqueous sodium hydrogen carbonate solution, and then once with saturated brine, followed by drying over sodium sulfate. The solution was concentrated to quantitatively obtain a sulfoxide.

To the resultant sulfoxide (6.85 mmol) was added acetic anhydride (34.2 ml), and the mixture was heated while stirring for 3 hours at 100° C. The mixture was allowed to cool, brought to dryness under reduced pressure, and purified by silica gel column chromatography (AcOEt:Hex= 1:10), thereby obtaining 1.79 of 1-O-acetyl-2,3,5-tri-O-benzyl-4-thio-D-arabinofuranose (yield: 56.5%).

Elementary analysis: for $C_{28}H_{30}O_4S.0.75H_2O$

Calculated C: 70.63, H: 6.67

Found C: 70.37, H: 6.24

$^1$H—NMR (CDCl$_3$) δ 7.35–7.24 (15H, m), 6.07 (1H, d, J=3.9 Hz), 5.98 (1H, d, J=2.9 Hz), 4. 83–4.48 (6H, m), 4.26 (1H, dd, J=2.9, 4.9Hz), 4.18 (1 H, dd, J=3.9, 8.8 Hz), 4.12 (1 H, dd, J =6.8, 8.8 Hz), 4.03 (1H, dd, J=4.9, 6.4 Hz), 3.76 (1H, m), 3.73–3.44 (2H, m), 3.40 (1H, m), 2.04 (3H, s)

5) Synthesis of [Ia-α]9-(4-thio-α-D-arabinofuranosyl)-2,6-diaminopurine and [Iaβ]9-(4-thio-β-D-arabinofuranosyl) -2,6-diaminopurine (in formula [I], B=2, 6-diaminopurine)

1-O-Acetyl-2,3,5-tri-O-benzyl-4-thio-D-arabinofuranose (800 mg, 1.67 mmol) was dissolved in distilled acetonitrile (7 ml). 2,6-Diaminopurine (452 mg) and molecular sieve 4A (897 mg) were added thereto. To the resultant mixture was added dropwise trimethylsilyl triflate (0.75 ml) at room temperature, and the mixture was stirred for 1 hour. Subsequently, a saturated aqueous sodium hydrogen carbonate solution was added, followed by stirring for 30 minutes to stop the reaction. The mixture was extracted with methylene chloride, and the organic layer was washed with a saturated aqueous sodium hydrogen carbonate solution, followed by drying over sodium sulfate. The residue was concentrated and purified by silica gel column chromatography (5% MeOH in CHCl$_3$). The resultant purified product (378 mg, 0.70 mmol) was dissolved in distilled methylene chloride (5 ml). 1.0 M Boron trichloride (4.2 ml) was added dropwise at −78° C. and the mixture was stirred for 1 hour. The mixture was further allowed to react for 2 hours at −20° C. The reaction was stopped using a saturated aqueous sodium hydrogen carbonate solution (1.05 g). The mixture was separated using methylene chloride, after which the aqueous layer was concentrated and desalted by silica gel column chromatography (CHCl$_3$:MeOH=5:1). Subsequently, the title compound was obtained via reverse phase HPLC.

[Ia-α] Melting point: 241–247 C. (H$_2$O)

UV $\lambda_{max}$ (H$_2$O) 281 nm (ε10300)

UV $\lambda_{max}$ (H$_2$O) 259 nm (ε9000)

Elementary analysis for $C_{10}H_{14}N_6O_3S.1H_2O$

Calculated C: 37.97, H: 5.10, N: 26.57

Found C: 37.90, H: 5.12, N: 26.39

$^1$H—NMR (DMSOd$_6$) δ8.00 (1H, s), 6.67 (2H, b r, D$_2$O exchangeable), 5.78 (2H, br, D$_2$ O exchangeable), 5.75 (1H, br, D$_2$O exchangeable ),5.58 (1 H, br, D$_2$O exchangeable), 5.56 (1H, d, J=7.3 Hz), 4.90 (1H, br, D$_2$exchangeable), 4.45 (1H, t, J=7.3 Hz), 3.86 (1H, dt, J=1.0, 11.0 Hz), 3.70 (1H, t, J=7.8 Hz), 3.6 3 (1H, m), 3.45 (1H, dt, J=8.1, 11.0 Hz)

[Ia-β] Melting point: 292–295° C. (H$_2$O)

UV $\lambda_{max}$ (H$_2$O) 282 nm (ε0400)

UV $\lambda_{max}$ (H$_2$O) 258 nm (ε8900)

Elementary analysis for $C_1H_{14}N_6O_3S.0.75H_2O$

Calculated C: 38.52, H: 5.01, N: 26.95

Found C: 38.82, H: 4.97, N: 26.89

$^1$H—NMR (DMSOd$_6$) δ7.93 (1H, s), 6.67 (2H, b r, D$_2$O exchangeable), 5.93 (1H, d, J=5.4 Hz) 5.74 (1H, d, J=4.9 Hz, D$_2$O exchangeable), 5. 51 (1H, d, J=4.9 Hz, D$_2$O exchangeable), 5.1 9 (1H, br, D$_2$O exchangeable), 4.12 (1H, dt, J=5.9, 6.8 Hz), 4.04 (1H, dt, J=5.4, 6.8 Hz), 3.83 (1H, dd, J=4.9, 10.7 Hz), 3.68 (1H, dd, J=6.8, 10.7 Hz), 3.22 (1H, ddd, J=4.9, 5.9, 6.8 Hz,)

Example 2:

Synthesis of [Ib-β]9-(4-thio-δ-D-arabinofuranosyl) guanine (in formula [I], B=guanine):

The procedure of Example 1–5) was repeated using 1-O-acetyl-2,3,5-tri-O-benzyl-4-thio-D-arabinofuranose and guanine, thereby obtaining the title compound. The target compound was also able to be obtained by treating the compound prepared in Example 1 with deaminase.

[Ib-β] Melting point: 260–264° C. (H$_2$O)

UV $\lambda_{max}$ (H$_2$O) 273 nm (ε9900)

UV $\lambda_{max}$ (H$_2$O) 256 nm (ε13200)

Elementary analysis for $C_{10}H_{13}N_5O_4S.1H_2O$

Calculated C: 37.85, H: 4.76, N: 22.07

Found C: 37.84, H: 4.76, N: 21.71

$^1$H—NMR (DMSOd$_6$) δ10.56 (1H, br), 7.92 (1H, s), 6.44 (2H, br, D$_2$O exchangeable), 5.86 (1H, d, J=5.4 Hz), 5.71 (1H, d, J=5.4 Hz, D$_2$O exchangeable), 5.49 (1H, d, J=4.9 Hz, D$_2$O exchangeable), 5.14 (1H, t, J=5.4 Hz, D$_2$O echangeable), 4.07 (1H, dd, J=5.4, 11.0 Hz), 4.03 (1H, dd, J=6.6, 11.0 Hz) 3.83 (1H, dt, J =5.4, 5.9 Hz), 3.67 (1H, dt, J=5.4, 5.9 Hz), 3.21 (1H, dt, J=5.4, 6.6 Hz)

Example 3:

Synthesis of [Ic-α]9-(4-thio-α-D-arabinofuranosyl) adenine and [Ic-β]9-(4-thio-β-D-arabinofuranosyl)adenine (in formula [I], B=adenine):

The procedure of Example 1–5) was repeated using 1-O-acetyl-2,3,5-tri-O-benzyl-4-thio-D-arabinofuranose and adenine, thereby obtaining the title compound.

[Ic-α] Melting point: 250° C. (H$_2$O)

UV λ$_{max}$ (H$_2$O) 261 nm (ε13600)

Elementary analysis for C$_{10}$H$_{13}$N$_5$O$_3$S$_1$
Calculated C: 42.40, H: 4.63, N: 24.72
Found C: 42.32, H: 4.60, N: 24.44

$^1$H—NMR (DMSOd$_6$) δ8.41 (1H, s), 8.15 (1H, s) 7.24 (2H, br, D$_2$O exchangeable), 5.79 (1H, d, J=4.9 Hz, D$_2$O exchangeable), 5.73 (1H, d, J=7.3 Hz), 5.61 (1H, d, J=4.4 Hz, D$_2$O exchangeale), 4.93 (1H, t, J=4.6 Hz, D$_2$O exchangeable), 4.56 (1H, dt, J=4.4, 7.3 Hz), 3.89 (1H, dt, J=3.9, 10.7 Hz), 3.75 (1H, dt, J=4. 4, 7.8 Hz), 3.66 (1H, ddd, J=3.9, 7.8, 8.1 Hz), 3.50 (1H, dt, J=8.1, 10.7 Hz)

[Ic-β] Melting point: 138–140° C. (H$_2$O)

UV λ$_{max}$ (H$_2$O) 261 nm (ε11800)

Elementary analysis for C$_{10}$H$_{13}$N$_5$O$_3$S$_1$.2H$_2$O
Calculated C: 37.61, H: 5.37, N: 21.93
Found C: 37.66, H: 5.37, N: 21.93

$^1$H—NMR (DMSOd$_6$) δ8.36 (1H, s), 8.13 (1H, s), 7.22 (2H, br, D$_2$O exchangeable), 6.05 (1H, d, J=5.4 Hz), 5.72 (1H, br, D$_2$O exchangeable ), 5.51 (1H, d, J=2.9 Hz, D$_2$O exchangeable), 5.19 (1H, br, D$_2$O exchangeable), 4.18–4.1 1 (2H, m), 3.87 (1H, dd, J=3.9, 11.2 Hz), 3.7 8 (1H, dd, J=6.6, 11.2 Hz), 3.25 (1H, ddd, J=3.9, 5.9, 6.6 Hz)

Example 4:

Synthesis of [Id-α]9-(4-thio-a-D-arabinofuranosyl)-2-aminopurine and [Id-β]9-(4-thio-p-D-arabinofuranosyl)-2-aminopurine (in formula [I], B=2-aminopurine):

The procedure of Example 1–5) was repeated using 1-O-acetyl-2,3,5-tri-0-benzyl-4-thio-D-arabinofuranose and 2-aminopurine, thereby obtaining the title compound.

[Id-α]

$^1$H—NMR (DMSOd$_6$) δ8.56 (1H, s), 8.37 (1H, s), 6.54 (1H, s), 5.81 (1H, d, J=5.9 Hz), 5.65 (1H, d, J=7.3 Hz), 5.62 (1H, d, J=4.9 Hz), 4.93 (1H, t, J=5.1 Hz), 4.47 (1H, dt, J=7.3 Hz), 3. 89 (1H, dt, J=3.4, 11.2 Hz), 3.72 (1H, dt, J=8.1 Hz), 3.64 (1H, dt, J=3.4, 8.1, 8.3 Hz), 3. 43 (1H, dt, J=8.3, 11.2 Hz)

[Id-β]

$^1$H—NMR (DMSOd$_6$) δ8.56 (1H, s), 8.29 (1H, s), 6.51 (2H, s), 6.00 (1H, d, J=4.9 Hz), 5.74 (1H, d, J=4.9 Hz), 5.50 (1H, d, J=4.4 Hz), 5.16 (1H, t, J=4.9 Hz), 4.10 (1H, dt, J=4.9, 5.9 H z), 3.92 (1H, dt, J=3.4, 11.2 Hz), 3.75 (1H, dt, J=5.9, 8.3 Hz), 3.70 (1H, dt, J=7.8, 8.3, 11.2 Hz), 3.51 (1H, dt, J=7.8, 11.2 Hz)

Example 5:

Synthesis of [Ie-α]7-(4-thio-α-D-arabinofuranosyl) adenine and [Ie-β]7-(4-thio-β-D-arabinofuranosyl)adenine (in formula [I], B=adenine):

The procedure of Example 1–5) was repeated using 1-O-acetyl-2,3,5-tri-O-benzyl-4-thio-D-arabinofuranose and silylated adenine (prepared via subjecting adenine and a catalytic amount of ammonium sulfate to refluxing in hexamethyldisilazane overnight), thereby obtaining the title compound.

[Ie-α] Melting point: 247–249° C. (H$_2$O)

UV λ$_{max}$ (H$_2$O) 275 nm (ε9000)

UV λ$_{max}$ (H$_2$O) 251 nm (sh, ε6000)

Elementary analysis for C$_{10}$H$_{13}$N$_5$O$_3$S$_1$.0.55H$_2$O
Calculated C: 40.96, H: 4.85, N: 23.88
Found C: 41.27, H: 5.22, N: 23.99

$^1$H—NMR (DMSOd$_6$) δ8.62 (1H, s), 8.22 (1H, s), 6.96 (2H, br, D$_2$O exchangeable), 6.01 (1H, br, D$_2$O exchangeable), 5.93 (1H, d, J=7.3 H z), 5.63 (1H, d, J=4.4 Hz, D$_2$O exchangeable), 5.03 (1H, t, J=5.1 Hz, D$_2$O exchangeable), 4. 16 (1H, dt, J=7.3, 8.3 Hz), 3.91 (1H, ddd, J=3.4, 5.1, 10.7 H z), 3.80 (1H, t, J=8.3 Hz), 3. 63 (1H, ddd, J=3.4, 7.8, 8.3 Hz), 3.53 (1H, d dd, J=5.1, 7.8, 10.7 Hz)

[Ie-β] Melting point: 163–167° C. (H$_2$O)

UV λ$_{max}$ (H$_2$O) 273 nm (ε8900)

UV λ$_{max}$ (H$_2$O) 249 nm (sh, ε6000)

Elementary analysis for C$_{10}$H$_{13}$N$_5$O$_3$S$_1$.0.75H$_2$O
Calculated C: 40.47, H: 4.92, N: 23.59
Found C: 40.83, H: 4.87, N: 23.64

$^1$H—NMR (DMSOd$_6$) δ68.89 (1H, s), 8.15 (1H, s) 6.80 (2H, br, D$_2$O exchangeable), 6.08 (1H d, J=5.9 Hz), 5.78 (1H, d, J=5.9 Hz, D$_2$O exchangeable), 5.46 (1H, d, J=5.9 Hz, D$_2$O exchangeable), 5.33 (1H, t, J=4.6 Hz, D$_2$O exchangeable), 4.14–4.10 (1H, m), 3.87–3.83 (1H, m), 3.81–3.79 (2H, m), 3.16 (1H, ddd, J=4.4, 7.8, 8.3 Hz)

Example 6:

Synthesis of [If-α]7-(4-thio-α-D-arabinofuranosyl)-2,6-diaminopurine and [If-β]7-(4-thio-β-D-arabinofuranosyl)-2, 6-diaminopurine (in formula [I], B=2,6-diaminopurine):

The procedure of Example 1–5) was repeated using 1-O-acetyl-2,3,5-tri-O-benzyl-4-thio-D-arabinofuranose and silylated 2,6-diaminopurine (prepared via subjecting 2,6-diaminopurine and a catalytic amount of ammonium sulfate to refluxing in hexamethyldisilazane overnight), thereby obtaining the title compound.

[If-α]

$^1$H—NMR (DMSOd$_6$) δ8.21 (1H, s), 6.49 (2H, s), 5.97 (1H, bs), 5.76 (1H, d, J=7.8 Hz), 5.62 (1H, bs), 5.59 (2H, s), 5.02 (1H, bs), 4.12 (1H, dt, J=8.3 Hz), 3.89 (1H, m), 3.58–3.49 (2H, m), 3.46 (1H, dt)

[If-β]

$^1$H—NMR (DMSOd$_6$) δ8.51 (1H, s), 6.30 (2H, s), 5.95 (1H, d, J=5.4 Hz), 5.44 (2H, s), 4.08 (1 H, dd, J=5.4 Hz), 3.86 (1H, dd, J=8.3 Hz),3. 78–3.72 (2H, dd×2, J=3.4, 4.9, 11.2 Hz),3. 13 (1H, dt, J=3.4, 4.9, 8.3 Hz)

Example 7:

Synthesis of [Ig-α]7-(4-thio-α-D-arabinofuranosyl)-2-aminopurine and [Ig-β]7-(4-thio-β-D-arabinofuranosyl)-2-aminopurine (in formula [I], B=2-aminopurine):

The procedure of Example 1–5) was repeated using 1-O-acetyl-2,3,5-tri-O-benzyl-4-thio-D-arabinofuranose and silylated 2-aminopurine (prepared via subjecting 2-aminopurine and a catalytic amount of ammonium sulfate to refluxing in hexamethyldisilazane overnight), thereby obtaining the title compound.

[Ig-α]

$^1$H—NMR (DMSOd$_6$) δ8.79 (1H, s), 8.42 (1H, s), 6.28 (2H, s), 5.93 (1H, bs), 5.70 (1H, d, J=7. 3 Hz), 5.65 (1H, bs), 4.99 (1H, bs), 4.23 (1H, dt, J=7.3, 7.8 Hz), 3.91 (1H, dt, J=3.4, 11. 2 Hz), 3.70 (1H, dt, J=7.8, 8.3 Hz), 3.66 (1H, m, J=3.4, 7.8, 8.3 Hz), 3.51 (1H, dt, J=7.8, 11.2 Hz)

[Ig-β]

$^1$H—NMR (DMSOd$_6$) δ8.76 (1H, s), 8.59 (1H, s), 6.14 (1H, s), 6.00 (1H, d, J=5.9 Hz), 5.69 (1H, d, J=5.4 Hz),5.45 (1H, d, J=5.4 Hz),5.26 (1H, t, J=4.9 Hz), 4.09 (1H, m), 3.93 (1H, m, J=5.9 Hz), 3.81 (1H, m, J=4.4 Hz), 3.77 (1H, m), 3.24 (1H, m)

Formulation Example 1: Tablets

| | |
|---|---|
| Compound of the invention | 30.0 mg |
| Microcrystalline cellulose | 25.0 mg |
| Lactose | 39.5 mg |
| Starch | 40.0 mg |
| Talc | 5.0 mg |
| Magnesium stearate | 0.5 mg |

Using the above components, tablets were prepared via a routine method.

Formulation Example 2: Capsules

| | |
|---|---|
| Compound of the invention | 30.0 mg |
| Lactose | 40.0 mg |
| Starch | 15.0 mg |
| Talc | 5.0 mg |

Using the above components, capsules were prepared via a routine method.

Formulation Example 3: Injection preparation

| | |
|---|---|
| Compound of the invention | 30.0 mg |
| Glucose | 100.0 mg |

The above components were dissolved in purified water for injection preparations, thereby obtaining an injection liquid.

Test Examples

Test Method (1) Anti-HSV-1 Activity and Anti-HSV-2 Activity

1. Human fibroblasts derived from fetal lungs were subjected to subculturing in Eagle MEM supplemented with 10% semi-fetal calf serum (Mitsubishi Chemical Corporation) at a 1:2–4 split every 4 days.

2. A suspension of cells obtained by splitting their parent cells (1:2) was seeded in a 12-well multi-plate (2 ml/well), followed by culturing for 4–5 days at 37° C. in a $CO_2$-incubator.

3. The culture liquid was discarded, and Hanks' MEM (250 μl) containing 50–150 PFU of VR-3 strain of HSV-1 or MS strain of HSV-2 was inoculated, and the virus was allowed to be adsorbed for 30 minutes at 37° C. Thereafter, the viral liquid was discarded.

4. A 2.5% serum-added Eagle MEM containing a test compound and 0.8% methylcellulose was added and the resultant mixture was incubated in a $CO_2$-incubator for 2–3 days at 37° C. Generally, a test compound is diluted in serial ½ log$_{10}$, and the maximal concentration is 10 μg/ml.

5. The culture liquid was discarded, and the cells were stained with a 0.5% crystal violet solution. Under a stereoscopic light microscope, the number of plaques in each well was counted. Using the equation below, the plaque formation inhibitory ratio (percent inhibition) was obtained.

Percent Inhibition=(1 −N$_1$/N$_2$)×100 wherein N$_1$ represents the number of plaques in wells containing the test compound and N$_2$ represents the number of plaques containing in the control well (which contains no test compound).

6. The plaque formation inhibitory ratio was plotted on a graph with respect to the concentration of the test compound (logarithmic representation). From this doseplaque inhibition curve, the concentration of the test compound exhibiting 50% inhibition was obtained (ED$_{50}$).

(2) Anti-Varicella Zoster Virus (VZV) Activity

1. Human fibroblasts derived from fetal lungs were subjected to subculturing in Eagle MEM supplemented with 10% semi-fetal calf serum (Mitsubishi Chemical Corporation) at a 1:2–4 split every 4 days.

2. A suspension of cells obtained by splitting their parent cells (1:2) was seeded in a 12-well multi-plate (2 ml/well), followed by culturing for 4–5 days at 37° C. in a $CO_2$-incubator.

3. The culture liquid was discarded, and 750 μl of a 5% serum-added Eagle MEM containing 50–100 PFU of Oka strain of VZV was inoculated, and the virus was allowed to be adsorbed for 1 hour at 37° C.

4. Without removing the virus, 750 μl of Hanks' MEM containing the test compound was added, and the resultant mixture was incubated in a $CO_2$-incubator at 37° C. Generally, a test compound is diluted in serial ½ log$_{10}$, and the maximal concentration is 10 μg/ml.

5. After culturing for 4–5 days, the culture liquid was discarded, and the cells were stained with a 0.5% crystal violet solution. Under a stereoscopic light microscope, the number of plaques in each well was counted. Using the equation used in (1) above, the plaque formation inhibitory ratio was obtained.

6. The plaque formation inhibitory ratio was plotted on a graph with respect to the concentration of the test compound (logarithmic representation). From this doseplaque inhibition curve, the concentration of the test compound exhibiting 50% inhibition was obtained (ED$_{50}$).

(3) Anti-Human Cytomegalovirus Activity

1. Human fibroblasts derived from fetal lungs were subjected to subculturing in Eagle MEM supplemented with 10% semi-fetal calf serum (Mitsubishi Chemical Corporation) at a 1:2–4 split every 4 days.

2. A suspension of cells obtained by splitting their parent cells (1:2) was seeded in a 12-well multi-plate (2 ml/well), followed by culturing for 4 days at 37° C. in a $CO_2$-incubator.

3. The culture liquid was discarded, and 750 μl of a 5% serum-added Eagle MEM containing 50–100 PFU of AD-169 strain of HCMV was inoculated, and the virus was allowed to be adsorbed for 1 hour at 37° C.

4. Without removing the virus, 750 μl of Hanks' MEM containing the test compound was added, and the resultant mixture was incubated in a $CO_2$-incubator at 37° C. for 4 days. Generally, a test compound is diluted in serial 1/2 log$_{10}$, and the maximal concentration is 10 μg/ml.

5. The medium was changed to a fresh 2.5% serum-added Eagle MEM containing 0.8% methylcellulose and the test compound having the same concentration, followed by culturing further for 4–5 days.

6. The culture liquid was discarded, and the cells were stained with May-Gruenwald's-Giemsa (×10). Under a stereoscopic light microscope, the number of plaques in each well was counted. Using the equation used in (1) above, the plaque formation inhibitory ratio was obtained.

7. The plaque formation inhibitory ratio was plotted on a graph with respect to the concentration of the test compound (logarithmic representation). From this doseplaque inhibition curve, the concentration of the test compound exhibiting 50% inhibition was obtained (ED$_{50}$).

The results of these tests are shown in Table 1 below.

TABLE 1

| Compound No. | ED$_{50}$ ($\mu$g/ml) | | | |
|---|---|---|---|---|
| | HSV-1 | HSV-2 | VZV | HCMV |
| Ia-β | 0.52 | 0.40 | 0.11 | 0.022 |
| Ib-β | 0.49 | 0.59 | 0.11 | 0.011 |

What is claimed is:

1. A purine 4'-thioarabinonucleoside compound represented by the following formula [I]:

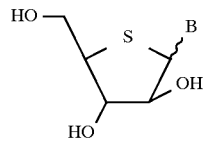

[I]

wherein B represents a purine base other than adenine.

2. A method for preparing purine 4'-thioarabinonucleoside of formula [I]:

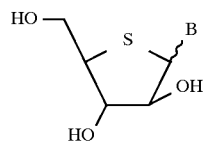

[I]

wherein B represents a purine base other than adenine, said method comprising the following steps 1 through 4:

Step 1:

introducing a sulfonyl group to each of the 2- and 5- positions of a compound of formula [II], and then reacting with a sulfide to obtain a compound represented by formula [III]:

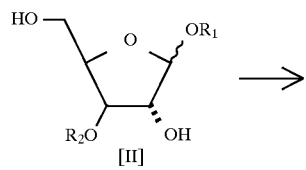

[II]

wherein $R_1$ represents an alkyl group and $R_2$ represents a protective group for a hydroxyl group, Step 2:

hydrolyzing the furanose ring of the compound represented by formula [III] followed by reduction to obtain a compound represented by formula [IV]:

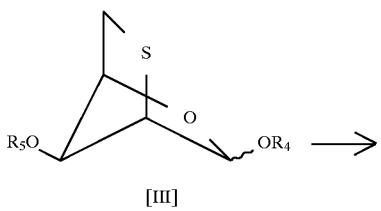

[III]

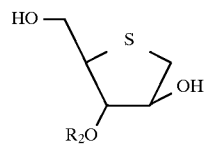

[IV]

wherein $R_1$ and $R_2$ have the same meanings as defined above,

Step 3:

reacting the compound of formula [IV], while protecting the hydroxyl groups at the 2- and 5- positions of the compound, with an oxidizing agent to form a sulfoxide, followed by conversion into a compound of formula [V] through Pummerer rearrangement:

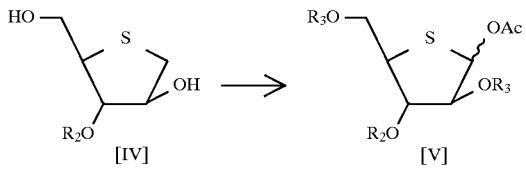

[IV]  [V]

wherein Ac represents an acetyl group and each of $R_2$ and $R_3$ represents a protective group for a hydroxyl group, and Step 4:

subjecting the compound of formula [V] to glycosylation reaction so as to introduce a purine base represented by B to the 1- position of the saccharide moiety, after which the protective groups for the hydroxyl groups in the saccharide moiety are eliminated to obtain a compound of formula [I]:

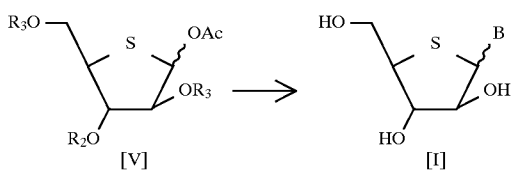

[V]  [I]

wherein Ac, $R_2$, $R_3$, and B have the same meanings as defined hereinbefore.

3. A pharmaceutical composition comprising as an active ingredient a purine 4'-thioarabinonucleoside compound described in claim 1 together with a carrier.

4. A method for treating a viral infection in a patient comprising administering to said patient an effective antiviral treatment amount of a compound of claim 1 or an effective antiviral treatment amount of a pharmaceutical composition containing as the active agent said compound together with a carrier.

5. The compound according to claim 1, wherein the compound is a β-anomer.

6. The compound according to claim 1, wherein the compound is a 9-glycosylated compound.

7. The compound according to claim 1, wherein the compound is a β-anomer 9-glycosylated compound.

8. The compound 9-(4-thio-β-D-arabinofuranosyl)-2,6-diaminopurine.

9. The compound 9-(4-thio-β-D-arabinofuranosyl) guanine.

* * * * *